(12) United States Patent
Kim et al.

(10) Patent No.: US 9,326,733 B2
(45) Date of Patent: May 3, 2016

(54) SYSTEM AND METHOD FOR ACQUISITION OF BIOPOTENTIAL SIGNALS WITH MOTION ARTIFACT REDUCTION IN REAL TIME OPERATION

(71) Applicant: IMEC VZW, Leuven (BE)

(72) Inventors: Hyejung Kim, Leuven (BE); Nick Van Helleputte, Korbeek Dijle (DE); Refet Firat Yazicioglu, Leuven (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 14/615,150

(22) Filed: Feb. 5, 2015

(65) Prior Publication Data

US 2015/0216481 A1 Aug. 6, 2015

(30) Foreign Application Priority Data

Feb. 6, 2014 (EP) .................................. 14154192

(51) Int. Cl.
*A61B 5/04* (2006.01)
*A61B 5/00* (2006.01)
*A61B 5/0402* (2006.01)
*A61B 5/0476* (2006.01)
*A61B 5/0488* (2006.01)

(52) U.S. Cl.
CPC ............. *A61B 5/7207* (2013.01); *A61B 5/0402* (2013.01); *A61B 5/04012* (2013.01); *A61B 5/04017* (2013.01); *A61B 5/0476* (2013.01); *A61B 5/0488* (2013.01); *A61B 5/7214* (2013.01)

(58) Field of Classification Search
CPC ........... A61B 5/04012; A61B 5/04017; A61B 5/0402; A61B 5/0476; A61B 5/0488; A61B 5/7207; A61B 5/7214

See application file for complete search history.

(56) References Cited

U.S. PATENT DOCUMENTS

2007/0002961 A1* 1/2007 Hoctor et al. .................. 375/267

FOREIGN PATENT DOCUMENTS

EP 2591720 A1 5/2013

OTHER PUBLICATIONS

European Search Report, European Patent Application No. 14154192.0, dated Jul. 11, 2014.
Liu, Xin et al., "An Ultra-Low Power ECG Acquisition and Monitoring ASIC System for WBAN Applications", IEEE Journal on Emerging and Selected Topics in Circuits and Systems, vol. 2, No. 1, Mar. 1, 2012, pp. 60-70.

(Continued)

*Primary Examiner* — George Manuel
(74) *Attorney, Agent, or Firm* — McDonnell Boehnen Hulbert & Berghoff LLP

(57) ABSTRACT

A biopotential signal acquisition system comprising an analog readout unit configured to receive an analog biopotential signal and to extract an analog measured biopotential signal and an analog reference signal, and an ADC unit configured to provide a digital version of the analog measured biopotential signal and the analog reference signal. The system also includes a first digital filter unit comprising a cascaded integrator-comb filter configured to provide a first digital filtered version of the digital measured biopotential signal and the reference signal, and a second digital filter unit configured to calculate a digital motion artifact estimate based on the first digital filtered version signals.

12 Claims, 2 Drawing Sheets

(56) References Cited

OTHER PUBLICATIONS

Srivastava, Ashok et al., "A Programmable Oversampling Sigma-Delta Analog-to-Digital Converter", 48th Midwest Symposium on Circuits and Systems, Aug. 7, 2005, pp. 539-542.

Kim, Sunyoung et al., "Real Time Digitally Assisted Analog Motion Artifact Reduction in Ambulatory ECG Monitoring System", 34th Annual International Conference of the IEEE EMBS, San Diego, California USA, Aug. 28-Sep. 1, 2012, pp. 2096-2099.

* cited by examiner

SYSTEM AND METHOD FOR ACQUISITION OF BIOPOTENTIAL SIGNALS WITH MOTION ARTIFACT REDUCTION IN REAL TIME OPERATION

CROSS-REFERENCE TO RELATED APPLICATION

This application claims priority to European Patent Application No. 14154192.0 filed on Feb. 6, 2014, the contents of which are hereby incorporated by reference

TECHNICAL FIELD

The present description relates generally to the field of biopotential signal acquisition systems and more specifically to a system and a method for acquisition of biopotential signals with motion artifact reduction using digital adaptive filtering.

BACKGROUND

Ambulatory monitoring of biopotential signals, such as electrocardiogram (ECG), electroencephalogram (EEG), electromyogram (EMG), etc., is a highly relevant topic in personal healthcare. On issue in such application environments is overcoming motion artifacts that may significantly affect recorded biopotential signals. One approach to reduce motion artifacts makes use of digital adaptive filtering. For example, a biomedical acquisition system with motion artifact reduction is disclosed in EP 2591720 A1, which uses digital adaptive filtering (e.g., an LMS filter), implemented in a digital domain, to calculate a motion artifact estimate that is then fed back to the analogue domain and subtracted from the measured ECG before final amplification.

SUMMARY

According to one aspect of the present description, a new biopotential signal acquisition system is provided with improved motion artifact reduction. According to other aspects, the system may also be advantageous for ambulatory and/or low power biopotential monitoring applications.

According to an example embodiment, there is provided a biopotential signal acquisition system that includes an analogue readout unit configured to receive an analogue biopotential signal and to extract an analogue measured biopotential signal and an analogue reference signal. The system also includes an ADC unit configured to provide a digital version of the analogue measured biopotential signal and the analogue reference signal, a first digital filter unit comprising a cascaded integrator-comb filter configured to provide a first digital filtered version of the digital measured biopotential signal and the reference signal, and a second digital filter unit configured to calculate a digital motion artifact estimate based on the first digital filtered version signals.

The analogue biopotential signal may be acquired, for example, from at least one electrode attached to a body. In one example, by calculating the digital motion artifact estimate using the digital filtered version of the signals at the output of the cascaded integrator-comb filter, the signal group delay is reduced. Furthermore, the convergence speed for calculating the motion artifact estimate in the second digital filter unit is reduced. Consequently, the system real-time response with motion artifact reduction may be improved. In addition, power consumption may be also reduced.

According to an example embodiment, the second digital filter unit implements or runs a digital adaptive filter.

According to an example embodiment, the cascaded integrator-comb filter has a sampling frequency higher than the frequency band of the digital adaptive filter.

According to an example embodiment, the digital adaptive filter is an LMS filter.

According to an example embodiment, the ADC unit comprises a Sigma-Delta ADC.

According to an example embodiment, the analogue reference signal is an electrode-tissue impedance signal.

According to an example embodiment, the analogue biopotential signal is an ECG signal.

According to an example embodiment, the system is implemented on a single integrated circuit.

According to an example embodiment, the calculated digital motion artifact estimate is converted to an analogue signal and fed to the analogue readout unit for motion artifact reduction.

According to an example embodiment, the first digital filter unit further comprises a halfband decimation filter and a finite impulse response filter connected to the cascaded integrator-com filter.

There is also provided and electronic device comprising a biopotential signal acquisition system according to any of the embodiments herein described.

There is also provided an example method for acquisition of biopotential signals that includes extracting, from an analogue biopotential signal, an analogue measured biopotential signal and an analogue reference signal, and converting the analogue measured biopotential signal and an analogue reference signal into digital signals. The method also may include filtering the digital measured biopotential signal and reference signal with a cascaded integrator-comb filter, and calculating a digital motion artifact estimate based on the digital filtered versions of the digital measured biopotential signal and the reference signal at the output of the cascaded integrator-comb filter.

According to an example embodiment, the method further comprises converting the digital motion artifact estimate into an analogue signal and using the analogue motion artifact estimate for extracting the measured biopotential signal.

Certain objects and advantages of various new and inventive aspects have been described above. It is to be understood that not necessarily all such objects or advantages may be achieved in accordance with any particular embodiment of the present description. Those skilled in the art will recognize that the example solution disclosed in the present description may be embodied or carried out in a manner that achieves or optimizes one advantage or group of advantages without necessarily achieving other objects or advantages.

BRIEF DESCRIPTION OF THE DRAWINGS

The above and other aspects of the system and method for acquisition of biopotential signals according to the present description will be shown and explained with reference to the non-restrictive example embodiments described hereinafter.

DETAILED DESCRIPTION

In the following, in the description of example embodiments, various features may be grouped together in a single embodiment, figure, or description thereof for the purpose of streamlining the disclosure and aiding in the understanding of one or more of the various inventive aspects. This is, however, not to be interpreted as the invention requiring more features than the ones expressly recited in the broadest claims. Furthermore, combinations of features of different embodiments are meant to be within the scope of the invention, as would be clearly understood by those skilled in the art. Additionally, in other instances, well-known methods, structures and techniques have not been shown in detail in order not to obscure the conciseness of the description.

Figure 1:
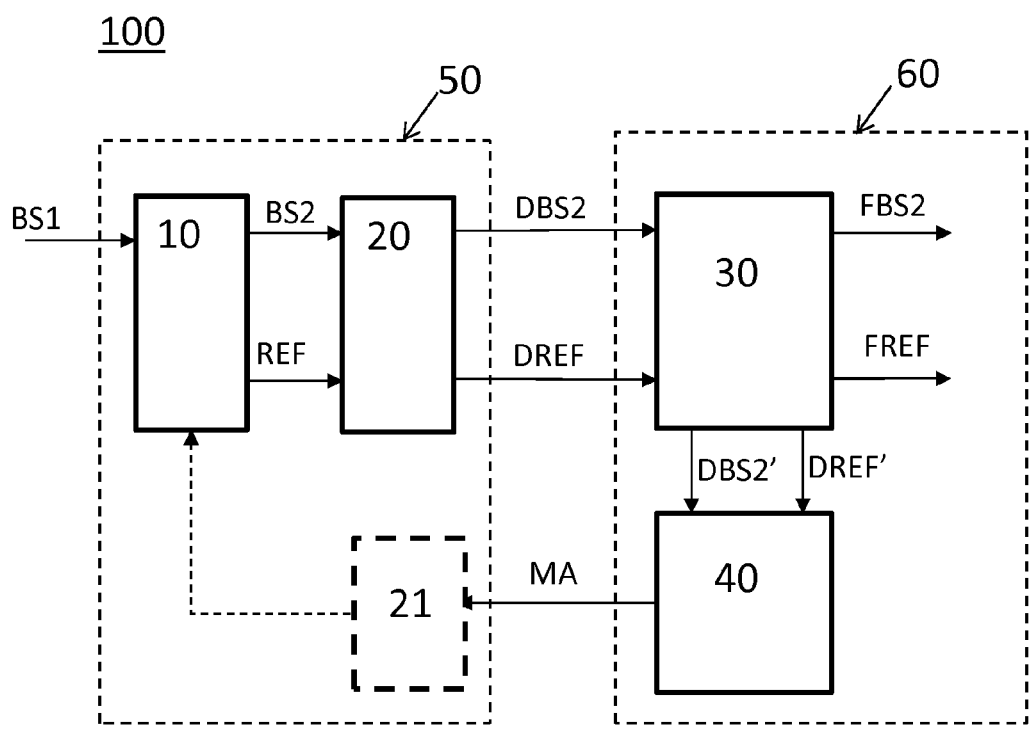
FIG. 1 shows a first example block diagram of a biopotential signal acquisition system.

FIG. 1 shows a first example block diagram of a biopotential signal acquisition system 100. The system comprises an analogue domain part 50 configured to receive at least one analogue biopotential signal BS1, which may be acquired, for example, from at least one sensor electrode attached to a living being body, and comprises an analogue readout unit 10 configured to extract at least one analogue measured biopotential signal BS2 and at least one analogue reference signal REF from the received analogue biopotential signal BS1. The analogue measured biopotential signal BS2 and the analogue reference signal REF are then provided to an analogue-to-digital converter (ADC) unit 20, which comprises one or more ADCs configured to convert those signals into digital versions DBS2, DREF, respectively, which are then handled in the digital domain part 60 of the system.

A first digital filter unit 30 receives the digital versions of the measured biopotential signal DBS2 and the reference signal DREF, and is configured to generate a digital filtered version of the measured biopotential signal FBS2 and the reference signal FREF. The first digital filter unit 30 may comprise, for that purpose, according to an embodiment, one or more cascaded integrator-comb filters 32, one or more halfband decimation filters 34 and one or more finite impulse response filters 36, as will be further described in relation to FIG. 2.

A second digital filter unit 40 is connected to the first digital filter unit 30 and receives intermediate digital filtered versions of the measured biopotential signal DBS2' and the reference signal DFREF', and is configured to calculate an estimated noise or motion artifact estimate MA. The motion artifact estimate MA may be used to reduce the motion artifact from the biopotential signal. According to an embodiment, the motion artifact estimate MA may be, for example, converted to an analogue signal and fed to the analogue readout unit 10 for motion artifact reduction in the analogue domain part 50.

According to an example embodiment, the second digital filter unit 40 may implement or run a digital adaptive filter, for example, a Least Mean Square (LMS) filter. But other types of digital adaptive filters may be implemented.

According to an example embodiment, the analogue-to-digital converter (ADC) unit 20 comprises a Sigma-Delta ADC. This may be advantageous since it increases the analogue-to-digital signal resolution of the acquisition system and the techniques herein described are particularly beneficial in combination with a Sigma-Delta ADC.

According to an example embodiment, the analogue biopotential signal BS1 is an electrocardiogram signal and the reference signal REF is an electrode-tissue impedance signal. Other reference signals could be used, such as for example, a galvanic skin response (GSR), a photoplethysmogram (PPG), or a bio impedance signal. Other biopotential signals may be also used.

According to an example embodiment, the first digital filter unit 30 and the second digital filter unit 40 may be implemented in hardware and/or software, in a dedicated digital domain part 60 and integrated in the same chip as the analogue part 50, for example, in analogue-digital mixed signal implementations. This may be advantageous, for example, to reduce the signal group delay and/or to reduce the power consumption for real-time biopotential signal acquisition applications.

Figure 2:
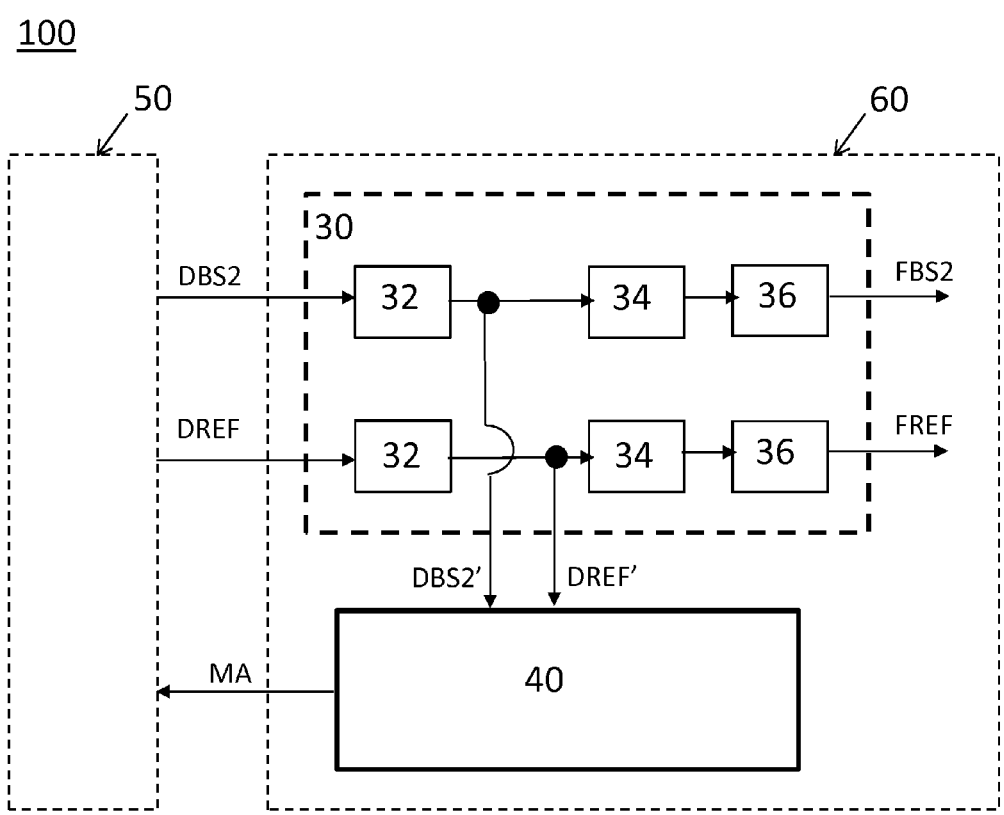
FIG. 2 shows a second example block diagram of a biopotential signal acquisition system.

FIG. 2 shows a second example block diagram of a biopotential signal acquisition system 100. Basically the same working principle as the one explained in relation to FIG. 1 applies, but the details of the first digital filter unit 30 are now shown. According to an embodiment, the first digital filter unit 30 may comprise one or more cascaded integrator-comb (CIC) filters 32, one or more halfband decimation (DEC) filters 34, and one or more finite impulse response (FIR) filters 36. This arrangement may be particularly suitable for post processing of the digital signals provided by the ADC, and more particularly, a Sigma-Delta ADC. In general, the filter chain of the first digital filter unit 30 serves for decimation, integration of the signal, and high frequency filtering. A different filter chain combination as the one shown in FIG. 2, for post processing of the digital signals, may be envisaged and is contemplated herein.

According to an example embodiment, the second digital filter unit 40 is connected to the output of the CIC filter 32, so that it receives a first digital filtered version DBS2', DREF' of the digital measured biopotential signal DBS2 and the reference signal DREF, respectively. The second digital filter unit 40 then uses those received signals DBS2', DREF' to calculate a motion artifact estimate MA.

According to an embodiment, the CIC filter 32 is designed with a sampling frequency that is higher than the frequency band of operation or final sampling frequency of the digital adaptive filter implemented in the second digital filter unit 40. Consequently, the digital adaptive filter operation may not be affected by frequency noise which lies above its frequency band of operation. According to an embodiment, the digital adaptive filter is designed to work as a low pass filter and therefore is generally not affected by high frequency noise. Accordingly, the digital adaptive filter can be advantageously directly connected to the CIC filter output. This may be beneficial, for example, to reduce the signal group delay and/or increase the convergence speed for calculating the motion artifact estimate and/or reduce the power consumption in real-time biopotential signal acquisition applications. According to an example embodiment, the CIC filter 32 has a sampling frequency of 1 KHz and the digital adaptive filter works at frequencies lower than 512 Hz.

Also advantageously, according to an embodiment, the system may enable a low-latency feedback of the motion artifact estimate MA to the analogue part 50. This may be particularly useful, for example, in mixed signal filter implementations.

We claim:

1. A biopotential signal acquisition system comprising:
   an analogue readout unit configured to receive an analogue biopotential signal and to extract an analogue measured biopotential signal and an analogue reference signal;
   a Sigma-Delta ADC unit configured to provide a digital measured biopotential signal from the analogue measured biopotential signal and a digital reference signal from the analogue reference signal;
   a first digital filter unit connected to an output of the Sigma-Delta ADC, and including a cascaded integrator-comb filter and a halfband decimation filter connected to the cascaded integrator-comb filter, wherein the first digital filter unit is configured to provide a first digital filtered version of the digital measured biopotential signal and the digital reference signal at an output of the cascaded integrator-comb filter, and a second digital filtered version of the digital measured biopotential signal and the digital reference signal at an output of the first digital filter unit; and a second digital filter unit connected to the output of the cascaded integrator-comb filter of the first digital filter unit, and configured to calculate a digital motion artifact estimate based on the first digital filtered version of the digital measured biopotential signal and the digital reference signal.

2. The biopotential signal acquisition system according to claim 1, wherein the second digital filter unit utilizes a digital adaptive filter.

3. The biopotential signal acquisition system according to claim 2, wherein the cascaded integrator-comb filter has a sampling frequency higher than a frequency band of the digital adaptive filter.

4. The biopotential signal acquisition system according to claim 2, wherein the digital adaptive filter is a Least Mean Square filter.

5. The biopotential signal acquisition system according to claim 1, wherein the analogue reference signal is an electrode-tissue impedance signal.

6. The biopotential signal acquisition system according to claim 1, wherein the analogue biopotential signal is an ECG signal.

7. The biopotential signal acquisition system according to claim 1, wherein the system is implemented on a single integrated circuit.

8. The biopotential signal acquisition system according to claim 1, wherein the calculated digital motion artifact estimate is converted to an analogue signal and fed to the analogue readout unit for motion artifact reduction.

9. The biopotential signal acquisition system according to claim 1, wherein the first digital filter unit further comprises a finite impulse response filter connected to the halfband decimation filter.

10. An electronic device comprising a biopotential signal acquisition system according to claim 1.

11. A method for acquisition of biopotential signals in a system according to claim 1, comprising:

extracting, from the analogue biopotential signal, the analogue measured biopotential signal and the analogue reference signal;

converting the analogue measured biopotential signal and the analogue reference signal into the digital measure biopotential signal and the digital reference signal, respectively;

filtering, with the cascaded integrator-comb filter, the digital measured biopotential signal and the digital reference signal to provide the first digital filtered version of the digital measured biopotential signal and the digital reference signal; and calculating the digital motion artifact estimate based on the first digital filtered version of the digital measured biopotential signal and the digital reference signal at the output of the cascaded integrator-comb filter.

12. The method for acquisition of biopotential signals according to claim 11, further comprising converting the digital motion artifact estimate into an analogue signal and using the analogue motion artifact estimate for extracting the measured biopotential signal.

* * * * *